US010111745B2

(12) United States Patent
Silvestrini et al.

(10) Patent No.: US 10,111,745 B2
(45) Date of Patent: Oct. 30, 2018

(54) ACCOMMODATING INTRAOCULAR LENS

(71) Applicant: LensGen, Inc., Irvine, CA (US)

(72) Inventors: Thomas Silvestrini, Alamo, CA (US); Ramgopal Rao, Irvine, CA (US)

(73) Assignee: LensGen, Inc., Irvine, CA (US)

( * ) Notice: Subject to any disclaimer, the term of this patent is extended or adjusted under 35 U.S.C. 154(b) by 169 days.

(21) Appl. No.: 14/936,544

(22) Filed: Nov. 9, 2015

(65) Prior Publication Data

US 2016/0128826 A1    May 12, 2016

Related U.S. Application Data

(63) Continuation of application No. 13/725,895, filed on Dec. 21, 2012, now Pat. No. 9,186,244.

(51) Int. Cl.
*A61F 2/16* (2006.01)

(52) U.S. Cl.
CPC .............. *A61F 2/1613* (2013.01); *A61F 2/16* (2013.01); *A61F 2/1616* (2013.01); *A61F 2/1629* (2013.01); *A61F 2/1635* (2013.01); *A61F 2/1648* (2013.01); *A61F 2002/169* (2015.04); *A61F 2250/0003* (2013.01); *A61F 2250/0004* (2013.01); *A61F 2250/0008* (2013.01)

(58) Field of Classification Search
CPC ........ A61F 2/16; A61F 2/1613; A61F 2/1616; A61F 2/1635; A61F 2250/0003; A61F 2250/0004; A61F 2250/0008
See application file for complete search history.

(56) References Cited

U.S. PATENT DOCUMENTS

| 4,373,218 A | 2/1983 | Schachar |
|---|---|---|
| 4,512,040 A | 4/1985 | McClure |
| 4,585,457 A | 4/1986 | Kalb |
| 4,720,286 A | 1/1988 | Bailey et al. |
| 4,731,078 A | 3/1988 | Stay et al. |
| 4,822,360 A | 4/1989 | Deacon |

(Continued)

FOREIGN PATENT DOCUMENTS

| EP | 0766540 B1 | 8/1999 |
|---|---|---|
| WO | WO2009015226 A3 | 1/2009 |

(Continued)

*Primary Examiner* — David Isabella
*Assistant Examiner* — Christine Nelson
(74) *Attorney, Agent, or Firm* — Sheppard Mullin Richter & Hampton LLP

(57) ABSTRACT

An accommodating intraocular lens (IOL) comprises an anterior lens, a posterior surface and an articulating member joining the anterior lens and the posterior surface to define an enclosed cavity. The articulating member comprises anterior and posterior arms coupling the anterior lens and the posterior surface, respectively. The articulating member further comprising a peripheral portion. A posterior flex region is disposed about the posterior arm and at a distance from the peripheral portion. The posterior flex region permits the flexible posterior surface to articulate relative to the posterior arm, to decrease the radius of curvature of the posterior surface as the peripheral portions on opposing sides of the IOL move toward one another in a first state and to increase the radius of curvature of the posterior surface as the peripheral portions on opposite sides of the IOL move away from one another in a second state.

18 Claims, 14 Drawing Sheets

(56) References Cited

U.S. PATENT DOCUMENTS

| | | |
|---|---|---|
| 4,842,601 A | 6/1989 | Smith |
| 4,888,012 A | 12/1989 | Horn et al. |
| 4,892,543 A | 1/1990 | Turley |
| 4,932,966 A | 7/1990 | Christie et al. |
| 5,035,710 A | 7/1991 | Nakada et al. |
| 5,091,121 A | 2/1992 | Nakada et al. |
| 5,275,623 A | 1/1994 | Sarfarazi |
| 5,443,506 A | 8/1995 | Garabet |
| 5,489,302 A | 2/1996 | Skottun |
| 5,607,472 A | 3/1997 | Thompson |
| 6,117,171 A | 9/2000 | Skottun |
| 6,730,123 B1 | 5/2004 | Klopotek |
| 6,855,164 B2 | 2/2005 | Glazier |
| 6,930,838 B2 | 8/2005 | Schachar |
| 7,063,723 B2 | 6/2006 | Ran |
| 7,122,053 B2 | 10/2006 | Esch |
| 7,217,288 B2 | 5/2007 | Esch et al. |
| 7,220,279 B2 | 5/2007 | Nun |
| 7,229,475 B2 | 6/2007 | Glazier |
| 7,247,168 B2 | 7/2007 | Esch et al. |
| 7,261,737 B2 | 8/2007 | Esch et al. |
| 7,416,562 B2 | 8/2008 | Gross |
| 7,438,723 B2 | 10/2008 | Esch |
| 7,453,646 B2 | 11/2008 | Lo |
| 7,485,144 B2 | 2/2009 | Esch |
| 7,637,947 B2 | 12/2009 | Smith et al. |
| 7,675,686 B2 | 3/2010 | Lo et al. |
| 7,753,953 B1 | 7/2010 | Yee |
| 7,776,088 B2 | 8/2010 | Shadduck |
| 7,815,678 B2 | 10/2010 | Nun |
| 7,842,087 B2 | 11/2010 | Nun |
| 7,854,764 B2 | 12/2010 | Nun |
| 7,857,850 B2 | 12/2010 | Mentak et al. |
| 7,981,155 B2 | 7/2011 | Cumming |
| 7,985,253 B2 | 7/2011 | Cumming |
| 7,998,199 B2 | 8/2011 | Nun |
| 8,018,658 B2 | 9/2011 | Lo |
| 8,034,106 B2 | 10/2011 | Mentak et al. |
| 8,034,107 B2 | 10/2011 | Stenger |
| 8,038,711 B2 | 10/2011 | Clarke |
| 8,048,155 B2 | 11/2011 | Shadduck |
| 8,052,752 B2 | 11/2011 | Woods et al. |
| 8,070,806 B2 | 12/2011 | Khoury |
| 8,158,712 B2 | 4/2012 | Your |
| 8,197,541 B2 | 6/2012 | Schedler |
| 8,216,306 B2 | 7/2012 | Coroneo |
| 8,254,034 B1 | 8/2012 | Shields et al. |
| 8,273,123 B2 | 9/2012 | Nun |
| 8,314,927 B2 | 11/2012 | Choi et al. |
| 8,320,049 B2 | 11/2012 | Huang et al. |
| 8,328,869 B2 | 12/2012 | Smiley et al. |
| 8,361,145 B2 | 1/2013 | Scholl et al. |
| 8,398,709 B2 | 3/2013 | Nun |
| 8,414,646 B2 | 4/2013 | De Juan, Jr. et al. |
| 8,425,599 B2 | 4/2013 | Shadduck |
| 8,447,086 B2 | 5/2013 | Hildebrand et al. |
| 8,454,688 B2 | 6/2013 | Esch et al. |
| 8,475,529 B2 | 7/2013 | Clarke |
| 8,545,556 B2 | 10/2013 | Woods et al. |
| 8,585,758 B2 | 11/2013 | Woods |
| 8,657,878 B2 | 2/2014 | Mentak et al. |
| 8,715,346 B2 | 5/2014 | De Juan, Jr. et al. |
| 8,734,509 B2 | 5/2014 | Mentak et al. |
| 8,814,934 B2 | 8/2014 | Geraghty et al. |
| 8,834,565 B2 | 9/2014 | Nun |
| 8,900,298 B2 | 12/2014 | Anvar et al. |
| 2003/0093149 A1 | 5/2003 | Glazier |
| 2003/0105522 A1 | 6/2003 | Glazier |
| 2003/0149480 A1 | 8/2003 | Shadduck |
| 2004/0082993 A1 | 4/2004 | Woods |
| 2004/0082994 A1 | 4/2004 | Woods et al. |
| 2004/0111153 A1 | 6/2004 | Woods et al. |
| 2004/0148023 A1 | 7/2004 | Shu |
| 2004/0162612 A1 | 8/2004 | Portney et al. |
| 2004/0169816 A1 | 9/2004 | Esch |
| 2004/0181279 A1 | 9/2004 | Nun |
| 2005/0071002 A1 | 3/2005 | Glazier |
| 2005/0107873 A1 | 5/2005 | Zhou |
| 2005/0119740 A1 | 6/2005 | Esch et al. |
| 2005/0137703 A1 | 6/2005 | Chen |
| 2005/0251253 A1 | 11/2005 | Gross |
| 2005/0251254 A1 | 11/2005 | Brady et al. |
| 2006/0041307 A1 | 2/2006 | Esch et al. |
| 2006/0047339 A1 | 3/2006 | Brown |
| 2006/0074487 A1 | 4/2006 | Gilg |
| 2006/0100701 A1 | 5/2006 | Esch et al. |
| 2006/0155372 A1 | 7/2006 | Coroneo |
| 2006/0212116 A1 | 9/2006 | Woods |
| 2007/0010880 A1 | 1/2007 | Esch |
| 2007/0021831 A1 | 1/2007 | Clarke |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0118216 A1 | 5/2007 | Pynson |
| 2007/0129798 A1 | 6/2007 | Chawdhary |
| 2007/0129799 A1 | 6/2007 | Schedler |
| 2007/0129800 A1 | 6/2007 | Cumming |
| 2007/0129801 A1 | 6/2007 | Cumming |
| 2007/0185574 A1 | 8/2007 | Nun |
| 2007/0203578 A1 | 8/2007 | Scholl et al. |
| 2007/0213817 A1 | 9/2007 | Esch et al. |
| 2007/0244561 A1 | 10/2007 | Nun |
| 2007/0260310 A1 | 11/2007 | Richardson |
| 2008/0004699 A1 | 1/2008 | Nun |
| 2008/0015689 A1 | 1/2008 | Esch et al. |
| 2008/0033547 A1 | 2/2008 | Chang et al. |
| 2008/0046074 A1 | 2/2008 | Smith et al. |
| 2008/0046075 A1 | 2/2008 | Esch et al. |
| 2008/0154364 A1 | 6/2008 | Richardson et al. |
| 2008/0188930 A1 | 8/2008 | Mentak et al. |
| 2008/0269887 A1 | 10/2008 | Cumming |
| 2008/0300680 A1 | 12/2008 | Nun |
| 2008/0306588 A1 | 12/2008 | Smiley et al. |
| 2008/0306589 A1 | 12/2008 | Donitzky et al. |
| 2009/0005865 A1 | 1/2009 | Smiley et al. |
| 2009/0027661 A1 | 1/2009 | Choi et al. |
| 2009/0149952 A1 | 6/2009 | Shadduck |
| 2009/0204210 A1 | 8/2009 | Pynson |
| 2009/0264998 A1 | 10/2009 | Mentak et al. |
| 2009/0292355 A1 | 11/2009 | Boyd et al. |
| 2009/0319040 A1 | 12/2009 | Khoury |
| 2010/0030332 A1 | 2/2010 | Schedler |
| 2010/0094412 A1 | 4/2010 | Wensrich |
| 2010/0121444 A1 | 5/2010 | Nun |
| 2010/0131058 A1 | 5/2010 | Shadduck |
| 2010/0179653 A1 | 7/2010 | Argento et al. |
| 2010/0211169 A1 | 8/2010 | Stanley et al. |
| 2010/0228344 A1 | 9/2010 | Shadduck |
| 2010/0288346 A1 | 9/2010 | Esch |
| 2010/0324672 A1 | 12/2010 | Esch et al. |
| 2010/0324674 A1 | 12/2010 | Brown |
| 2011/0029074 A1 | 2/2011 | Reisin et al. |
| 2011/0082544 A1 | 4/2011 | Nun |
| 2011/0112636 A1 | 5/2011 | Nun |
| 2011/0118834 A1 | 5/2011 | Lo et al. |
| 2011/0160852 A1 | 6/2011 | Mentak et al. |
| 2011/0224788 A1 | 9/2011 | Webb |
| 2011/0282442 A1 | 11/2011 | Scholl et al. |
| 2011/0288638 A1 | 11/2011 | Smiley et al. |
| 2012/0035724 A1 | 2/2012 | Clarke |
| 2012/0071972 A1 | 3/2012 | Zhao |
| 2012/0078361 A1 | 3/2012 | Shadduck |
| 2012/0078364 A1 | 3/2012 | Stenger |
| 2012/0150292 A1 | 6/2012 | Mentak et al. |
| 2012/0290084 A1 | 11/2012 | Coroneo |
| 2012/0296423 A1 | 11/2012 | Caffey |
| 2012/0296424 A1 * | 11/2012 | Betser .............. A61F 2/1613 623/6.13 |
| 2012/0310343 A1 * | 12/2012 | Van Noy .......... A61F 2/1635 623/6.39 |
| 2013/0006353 A1 | 1/2013 | Betser et al. |
| 2013/0018461 A1 | 1/2013 | Nun |
| 2013/0035760 A1 | 2/2013 | Portney |
| 2013/0131794 A1 | 5/2013 | Smiley et al. |

(56) References Cited

U.S. PATENT DOCUMENTS

| | | |
|---|---|---|
| 2013/0150960 A1* | 6/2013 | DeBoer .................. A61L 27/48 623/6.13 |
| 2013/0190867 A1 | 7/2013 | Peyman |
| 2013/0226295 A1 | 8/2013 | De Juan, Jr. et al. |
| 2013/0231741 A1 | 9/2013 | Clarke |
| 2013/0250239 A1 | 9/2013 | Hildebrand et al. |
| 2013/0268070 A1 | 10/2013 | Esch et al. |
| 2013/0317607 A1* | 11/2013 | DeBoer ................. A61F 2/1635 623/6.13 |
| 2014/0012277 A1 | 1/2014 | Matthews et al. |
| 2014/0135918 A1 | 5/2014 | De Juan, Jr. et al. |
| 2014/0249625 A1 | 9/2014 | Shadduck |

FOREIGN PATENT DOCUMENTS

| | | |
|---|---|---|
| WO | WO2011/137191 A1 | 11/2011 |
| WO | WO2013016804 A1 | 2/2013 |

* cited by examiner

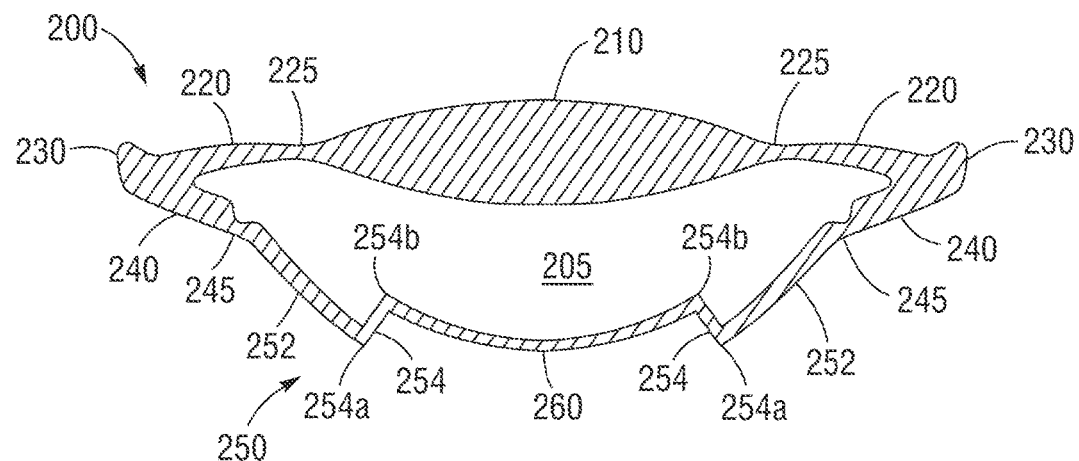
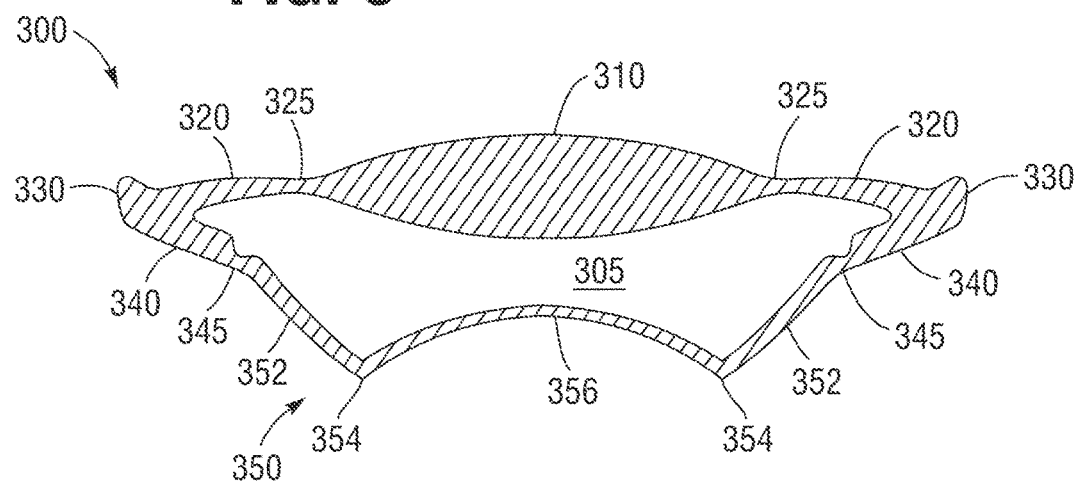

ACCOMMODATING INTRAOCULAR LENS

CROSS-REFERENCE TO RELATED APPLICATION

This application is a continuation of U.S. patent application Ser. No. 13/725,895, filed Dec. 21, 2012, the entire contents of which are incorporated herein by reference as if fully set forth herein.

FIELD OF THE INVENTION

The invention relates generally to an accommodating intraocular lens device and, more particularly, to an accommodating intraocular lens device configured for implantation in a lens capsule of a subject's eye.

BACKGROUND

Surgical procedures on the eye have been on the rise as technological advances permit for sophisticated interventions to address a wide variety of ophthalmic conditions. Patient acceptance has increased over the last twenty years as such procedures have proven to be generally safe and to produce results that significantly improve patient quality of life.

Cataract surgery remains one of the most common surgical procedures, with over 16 million cataract procedures being performed worldwide. It is expected that this number will continue to rise as average life expectancies continue to increase. Cataracts are typically treated by removing the crystalline lens from the eye and implanting an intraocular lens ("IOL") in its place. As conventional IOL devices are primarily focused for distance visions, they fail to correct for presbyopia and reading glasses are still required. Thus, while patients who undergo a standard IOL implantation no longer experience clouding from cataracts, they are unable to accommodate, or change focus from near to far, from far to near, and to distances in between.

Surgeries to correct refractive errors of the eye have also become extremely common, of which LASIK enjoys substantial popularity with over 700,000 procedures being performed per year. Given the high prevalence of refractive errors and the relative safety and effectiveness of this procedure, more and more people are expected to turn to LASIK or other surgical procedures over conventional eyeglasses or contact lens. Despite the success of LASIK in treating myopia, there remains an unmet need for an effective surgical intervention to correct for presbyopia, which cannot be treated by conventional LASIK procedures.

As nearly every cataract patient also suffers from presbyopia, there is convergence of market demands for the treatment of both these conditions. While there is a general acceptance among physicians and patients of having implantable intraocular lens in the treatment of cataracts, similar procedures to correct for presbyopia represent only 5% of the U.S. cataract market. There is therefore a need to address both ophthalmic cataracts and/or presbyopia in the growing aging population.

BRIEF SUMMARY

In one embodiment, an accommodating intraocular lens (IOL) is provided. The IOL comprises an anterior lens, a posterior surface, and an articulating member joining the anterior lens and the posterior surface. The articulating member comprises anterior and posterior arms coupling the anterior lens and the posterior surface, respectively. The articulating member further comprises a peripheral portion. A posterior flex region is disposed about the posterior arm and at a distance from the peripheral portion. The posterior flex region permits the flexible posterior surface to articulate relative to the posterior arm, to decrease the radius of curvature of the posterior surface as the peripheral portions on opposing sides of the IOL move toward one another in a first state and to increase the radius of curvature of the posterior surface as the peripheral portions on opposite sides of the IOL move away from one another in a second state.

In accordance with a first aspect, the anterior lens, the posterior surface and the articulating member define an enclosed cavity and the outer surface of the anterior lens and the posterior surface form a substantially biconvex shape when the enclosed cavity is filled with a fluid.

In accordance with a second aspect, the anterior lens has a convex outer surface and the posterior surface has a concave outer surface.

In accordance with a third aspect, the articulating member has a wishbone shape and the anterior and posterior arms are movable in reciprocating.

In accordance with a fourth aspect, the articulating member further comprises an anterior flex region between the anterior lens and the anterior arm.

In accordance with a fifth aspect, the anterior flex region permits displacement of the anterior lens in an anterior direction when the IOL is in the first state.

In accordance with a sixth aspect, the anterior flex region has a reduced thickness as compared to either one or both of the anterior arm and the anterior lens.

In accordance with a seventh aspect, the posterior flex region is disposed between the flexible posterior surface and the posterior arm.

In accordance with an eighth aspect, the posterior flex region has a reduced thickness as compared to either one or both of the posterior arm and the flexible posterior surface.

In accordance with a ninth aspect, one or both of the anterior and posterior flex regions is/are groove(s) disposed circumferentially about the IOL.

In accordance with a tenth aspect, the peripheral portion has a thickness that is greater than the thickness of the anterior or posterior arms.

In accordance with an eleventh aspect, the peripheral portion defines an outer circumference of the IOL.

In accordance with a twelfth aspect, the articulating member resiliently biases the IOL in either one of the first state or the second state.

In accordance with a thirteenth aspect, the thickness of the posterior surface decreases radially from the outer to the center of the posterior surface.

In accordance with a fourteenth aspect, the IOL further comprises a resilient spacer coupled to the peripheral portion, the resilient spacer being configured to articulate between a contracted state and an expanded state to decrease and to increase, respectively, a diameter of the IOL. The diameter of the IOL is defined with respect to the overall diameter, including the resilient spacer.

In accordance with a fifteenth aspect, the resilient spacer surrounds the entire peripheral portion of the IOL.

In accordance with a sixteenth aspect, the resilient spacer comprises a plurality of radial arms projecting from the peripheral portion of the IOL.

In another embodiment, an accommodating intraocular lens (IOL) described. The IOL comprises an anterior lens, a posterior surface, and an articulating member joining the anterior lens and the posterior surface to form an enclosed cavity. The articulating member comprises anterior and posterior rings coupling the anterior lens and the posterior surface, respectively, to a peripheral portion. A first hinge is disposed between the anterior lens and the anterior ring and a second hinge is disposed between the posterior surface and the posterior ring.

In accordance with a first aspect, the first and second hinges have a decreased thickness as compared to the thickness of one or both of the anterior and posterior rings.

In accordance with a second aspect, the second hinge is a circumferential groove defining a circular area having a diameter.

In accordance with a third aspect, the IOL is configured to articulate between a first and second state.

In accordance with a fourth aspect, the peripheral portions on opposing sides of the IOL move towards one another to cause a decrease in the radius of curvature of the posterior surface in a first state.

In accordance with a fifth aspect, the peripheral portions on opposing sides of the IOL move away from one another to increase the radius of curvature of the posterior surface in a second state.

In accordance with a sixth aspect, the anterior lens and a portion of the posterior surface surrounding an optical axis each have a concave exterior surface.

In accordance with a seventh aspect, the anterior lens and a portion of the posterior surface surrounding an optical axis define a biconvex exterior surface.

In accordance with a eighth aspect, the portion of the posterior surface is stepped into the enclosed cavity.

In accordance with a ninth aspect, the IOL further comprises a plurality of holes disposed on the anterior ring.

In accordance with a tenth aspect, the enclosed cavity comprises separate inner and outer circumferential cavities and an expandable bellow that separates the inner and outer circumferential cavities.

In accordance with an eleventh aspect, only the outer circumferential cavity is in fluid communication externally of the IOL through the plurality of holes.

In accordance with a twelfth aspect, the expandable bellow comprises a light-absorbing material.

In accordance with a thirteenth aspect, the IOL further comprises an expandable membrane defining an external cavity and wherein enclosed cavity is in fluid communication with the external cavity through the plurality of holes.

In a further embodiment, an accommodating intraocular lens (IOL) configured for implantation in a lens capsule of a patient's eye is described. The IOL comprises a refractive anterior lens, a deformable posterior membrane, and an articulating member joining the refractive anterior lens and the posterior membrane to form an enclosed cavity. The articulating member comprises an anterior portion, a posterior portion, and a peripheral portion. The anterior portion has one end coupling the anterior lens and the other end coupling the peripheral portion. The posterior portion has one end coupling the posterior membrane and the other end coupling the peripheral portion. In a first state, opposing sides of the peripheral portion move toward one another to displace the anterior lens in an anterior direction and causing the radius of curvature of the posterior membrane to increase. In a second state, opposing sides of the peripheral portion move away from one another, displacing the anterior lens in a posterior direction and causing the radius of curvature of the posterior membrane to decrease.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Illustrative embodiments of the present disclosure are described herein with reference to the accompanying drawings, in which:

FIG. 7 is a cross-sectional view of another embodiment of an IOL device;

FIG. 8 is a cross-sectional view of a further embodiment of an IOL device;

DETAILED DESCRIPTION OF THE PREFERRED EMBODIMENTS

Figure 1:
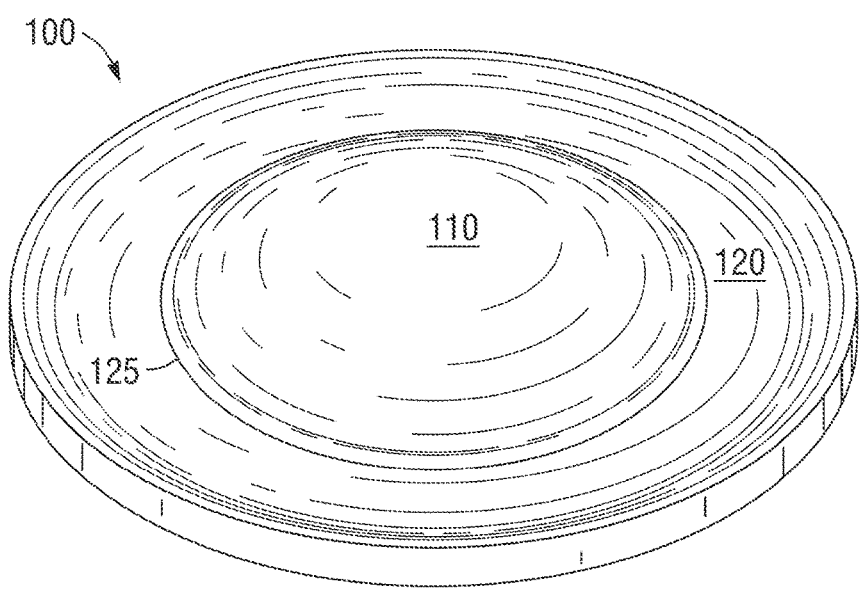
FIG. 1 is a top perspective view of one embodiment of the accommodating IOL device.
Figure 2:
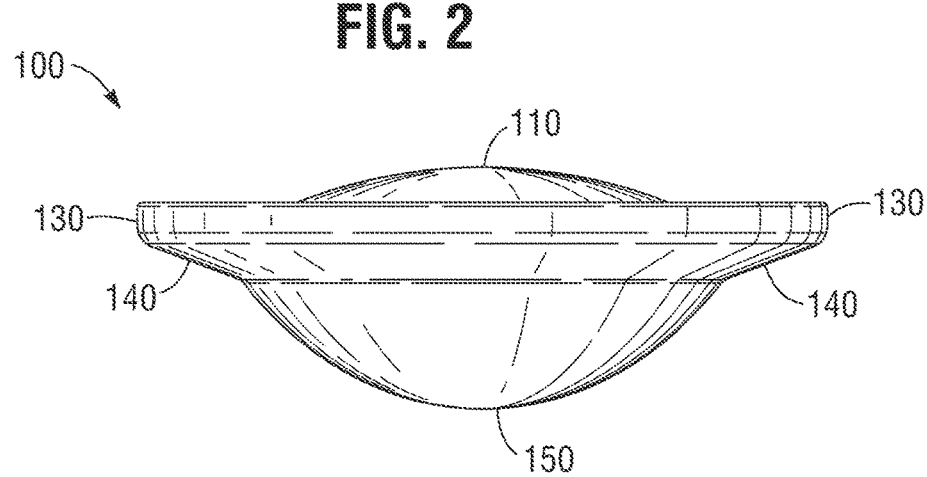
FIG. 2 is a side view of an embodiment of the accommodating IOL device.
Figure 3:
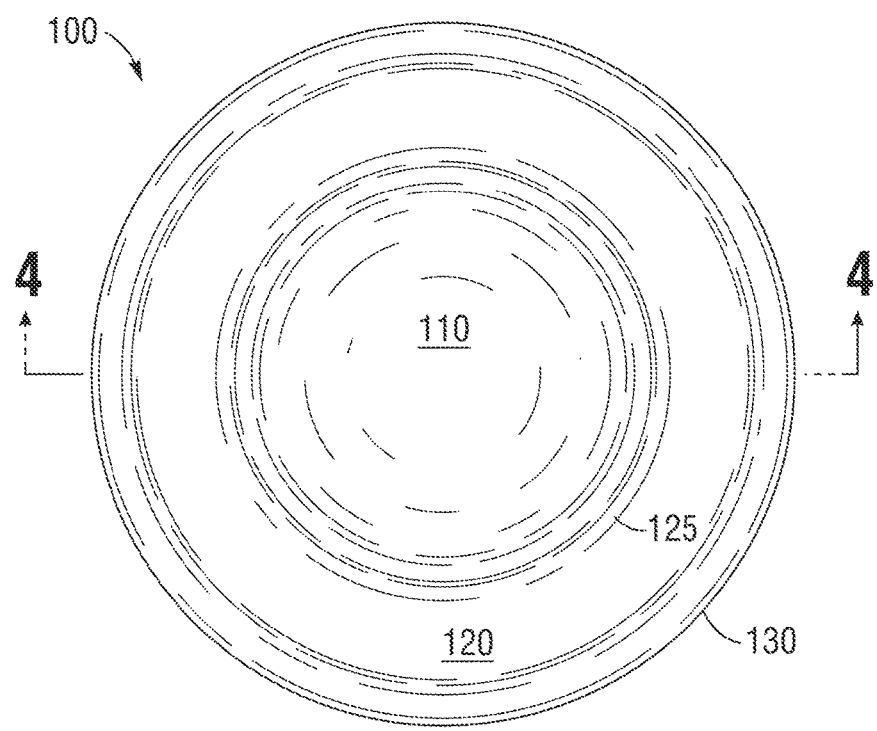
FIG. 3 is a top view of an embodiment of the accommodating IOL device.

Specific, non-limiting embodiments of the present invention will now be described with reference to the drawings. It should be understood that such embodiments are by way of example and are merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

FIGS. 1-4 illustrate a first set of embodiments of an accommodating IOL device 100 that may be implanted into the lens capsule 30 (see FIGS. 5 and 6) of the eye following cataract removal. The IOL device 100 is shown to comprise an anterior lens 110, a posterior surface 150 and an articulating member coupling the anterior lens 110 and the posterior surface 150 together. The articulating member is depicted as comprising an anterior member 120, a posterior member 140 and a peripheral portion 130 therebetween. In a preferred embodiment, the peripheral portion 130 defines the circumference of the IOL device 100.

The accommodating IOL device 100 is depicted in FIGS. 1-4 as having a biconvex exterior surface when the enclosed cavity 105 is filled with a fluid. In one embodiment, the fluid is a polyphenyl ether ("PPE"), as described in U.S. Pat. No. 7,256,943, entitled "Variable Focus Liquid-Filled Lens Using Polyphenyl Ethers" to Teledyne Licensing, LLC, the contents of which are incorporated herein by reference in its entirety. The advantages of utilizing PPE in the enclosed cavity is that such fluids provide twice the refractive power of water, exhibit a low absorption into and evaporation out of the elastomer membrane, do not readily form air bubbles, and have a low density and low viscosity. In another embodiment, the fluid may be selected from a viscoelastic fluid, an aqueous solution of saline and/or hyaluronic acid, or a fluid having the same viscosity as either one of the aqueous humor or the vitreous humor. Examples of different types of fluids that may be used in an implantable intraocular lens is described in WO 2011/137191, entitled Accommodating Intraocular Lens Device, the entire contents of which are incorporated herein by reference.

Figure 4A:
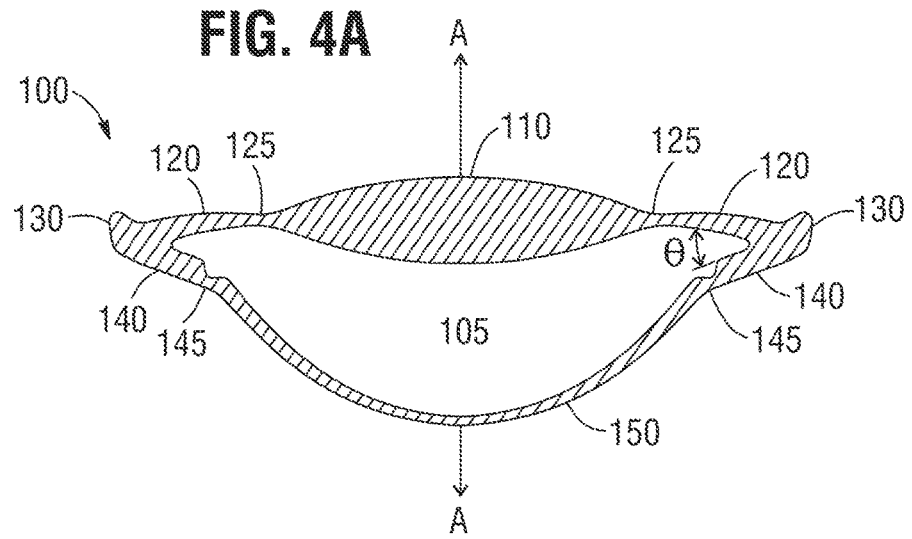
FIG. 4A is a cross-section view of an embodiment of the accommodating IOL device of FIG. 3 along the 4-4 axis.
Figure 4B:
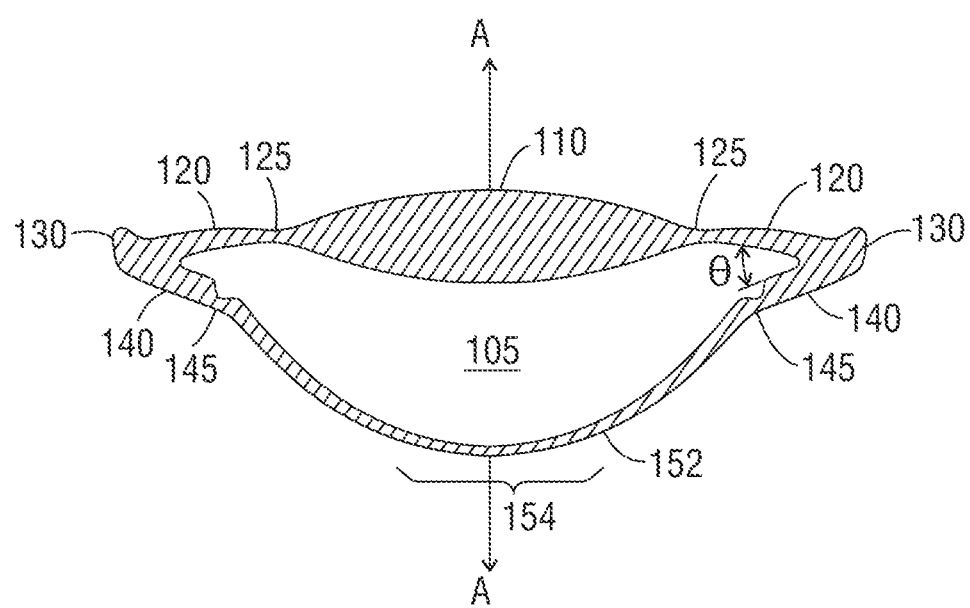
FIG. 4B is a cross-sectional view of an alternative embodiment of the accommodating IOL device of FIG. 3 along the 4-4 axis.
Figure 4C:
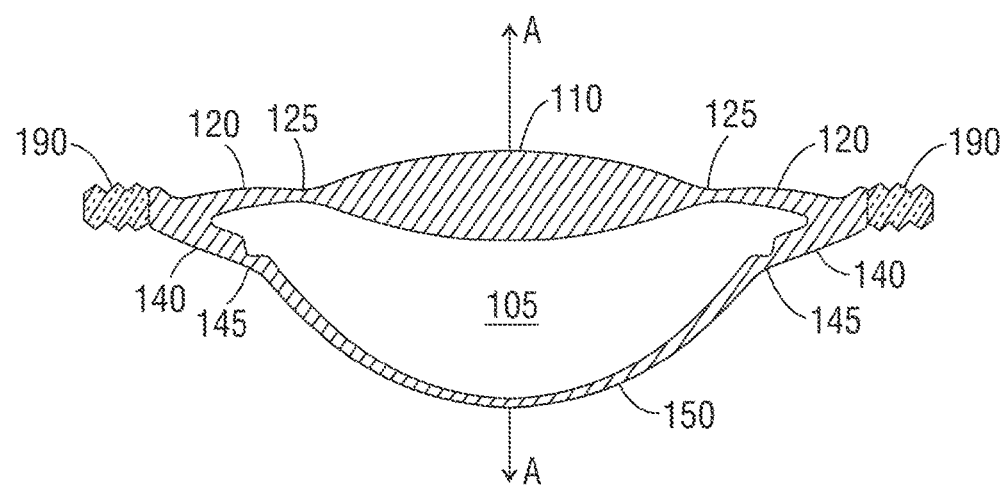
FIG. 4C is a cross-sectional view of another embodiment of the accommodating device having a contractable peripheral spacer about the periphery of the IOL device of FIG. 4B.

FIGS. 4A-C depict three different embodiments of the accommodating IOL device 100. As shown in each of these figures, the articulating member is depicted as having a wishbone shape in cross-section. The IOL device 100 further has a plurality of flex regions or hinges to permit the anterior lens 110 and the posterior surface 150 to reciprocate away and towards one another along an optical axis A-A. The inclusion of an anterior flex region or hinge 125 between the anterior lens 110 and the anterior portion 120 and a posterior flex region or hinge 145 between the posterior portion 140 and the posterior surface 150 permit a greater degree of displacement along the optical axis in opposing directions when opposing sides of the peripheral portion 130 move towards one another. Both the anterior member 120 and the posterior member 140 are angled away from one another so as to facilitate a reciprocal displacement away from and toward one another in response to the accommodating forces of the eye.

The posterior surface 150 of the IOL device 100 may be of uniform thickness (FIG. 4A) or may have a decreased thickness in the area surrounding the optical axis (FIG. 4B, 154). As shown in FIG. 4C, the IOL device 100 may further comprise a resilient spacer 190 that extends from the articulating member so as to permit the IOL device 100 to be adjustably sized to a range of different lens capsule sizes. The diameter of the IOL illustrated in FIG. 4C is therefore defined as the total diameter, including the spacer 190. In a preferred embodiment, the spacer 190 is made of a foam, such as a polymer foam, or other porous material that is capable of expanding or contracting its length so as to accommodate or adjust to the diameter of the natural lens capsule 30 after implantation. In one embodiment, the spacer 190 may further be loaded with drugs, biologic or other agents for treatment, to promote tissue ingrowth or adhesion, or to promote or reduce the contraction of the natural lens capsule 30 after implantation. Alternatively or additionally, the spacer 190 may be loaded with agents that are laser or light activated to stiffen after implantation in the lens capsule such that the diameter of the accommodating IOL device 100 that is implanted in the natural lens capsule 30 is substantially fixed.

The accommodating IOL device 100 may be made of a variety of elastomeric materials. In one embodiment, the device 100 may be made entirely of a single elastomeric material. In another embodiment, the articulating member, which comprises the anterior arm 120, the peripheral portion and the posterior arm 140, may be made of a different material than the anterior lens 110 and/or the posterior surface 150. Alternatively, the articulating member may be made of the same material but having different mechanical and physical characteristics than either one or both of the anterior lens 110 and the posterior surface 150.

In accordance with one aspect, the articulating member may be made of a shape memory material which is resiliently biased to maintain an angle θ in the absence of any force or pressure applied onto the peripheral portion 130 of the IOL device 100. The angle θ may increase and decrease based on the relaxation and contraction, respectively, of the ciliary muscles when the IOL device 100 is implanted in the lens capsule 30 of the eye.

In accordance with another aspect, the articulating member may be made of a rigid material such that the anterior arm 120 and the posterior arm 140 do not articulate relative to one another. In accordance with this aspect, the angle θ remains substantially constant after implantation and during the relaxation and contraction of the ciliary muscles. As angle θ remains constant, there is a greater deflection of the anterior lens 110 and the posterior portion 150 about the anterior flex region or hinge 125 and the posterior flex region or hinge 145 when the ciliary muscles relax and contract. Moreover, having a rigid articulating member will translate into a greater change in curvature of the anterior lens 110 and the posterior portion 150 as compared to the embodiment in which the angle θ changes, in response to the relaxation and contraction of the ciliary muscles.

Figure 5:
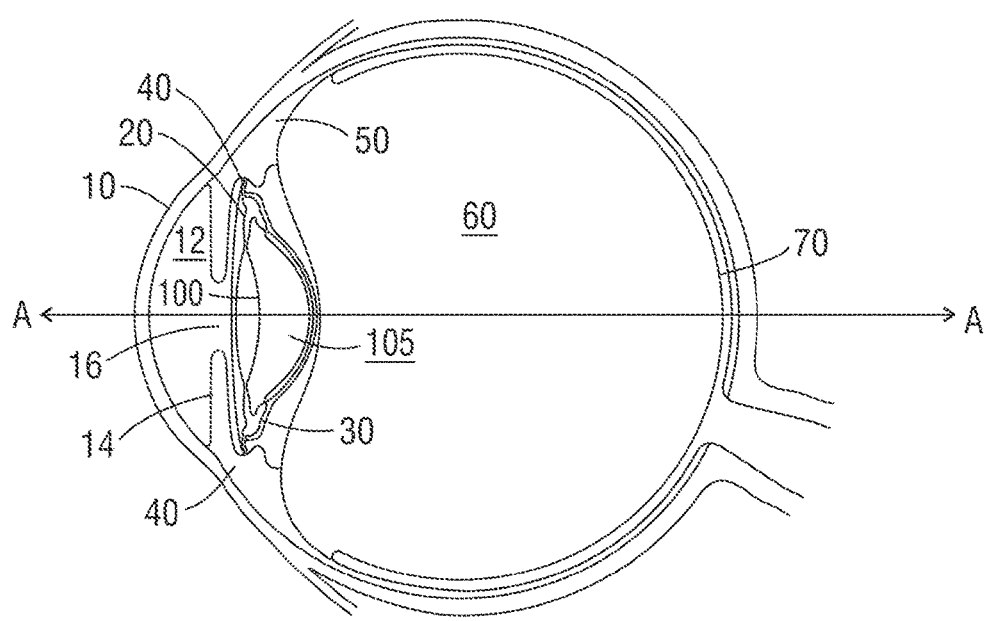
FIG. 5 is a sectional view illustrating certain anatomical features of the human eye with the IOL device of FIG. 4B implanted in the lens capsule in which the ciliary muscles of the eye are contracted.
Figure 6:
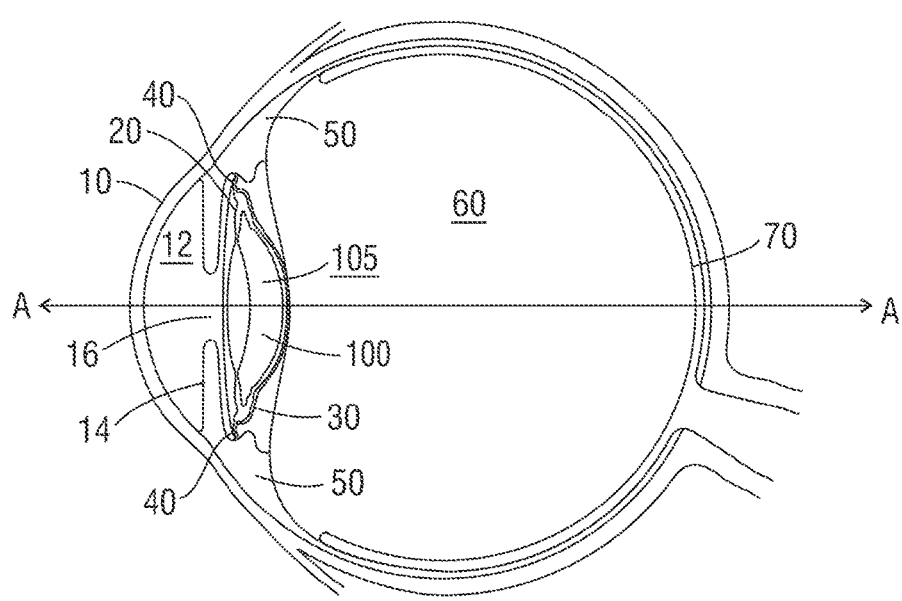
FIG. 6 is a sectional view illustrating certain anatomical features of the human eye with the IOL device of FIG. 4B implanted in the lens capsule in which the ciliary muscles of the eye are relaxed.

FIGS. 5-6 depict the accommodating IOL device 100 implanted in the natural lens capsule 30 of the eye.

Turning first to the relevant anatomical features of the eye, the lens is a clear, elastic structure that is housed within a lens capsule 30 and maintained under tension via the ciliary muscles 50 which are coupled to the lens capsule 30 via zonule fibers 40. As a result, the lens naturally tends towards a rounder configuration, a shape it must assume for the eye to focus at a near distance.

The human eye comprises three chambers of fluid: the anterior chamber 12, the posterior chamber 20 and the vitreous chamber 60. The anterior chamber 12 corresponds generally to the space between the cornea 10 and the iris 14 and the posterior chamber 20 corresponds generally to the space bounded by the iris 14, the lens capsule 30 and the zonule fibers 40 connected to the periphery of the lens capsule 30. The anterior chamber 12 and the posterior chamber 20 contain a fluid known as the aqueous humor, which flows therebetween through an opening that is defined by the iris 14, known as the pupil 16. Light enters the eye through the pupil 16 and travels along the optical axis A-A, striking the retina 7 and thereby producing vision. The iris 14 regulates the amount of light entering the eye by controlling the size of the pupil 16.

The vitreous chamber 60 is located between the lens capsule 30 and the retina 70 and contains another fluid, known as the vitreous humor. The vitreous humor is much more viscous than the aqueous humor and is a transparent, colorless, gelatinous mass. Although much of the volume of the vitreous humor is water, it also contains cells, salts, sugars, vitrosin, a network of collagen type II fibers with glycosaminoglycan hyaluronic acid, and proteins. The vitreous has a viscosity that is two to four times that of pure water, giving it a gelatinous consistency. It also has a refractive index of 1.336.

Implantation of the IOL device 100 is accomplished by first removing the natural lens housed within the lens capsule 30 through a small incision using standard surgical procedures, such as phago-emulsification. After removal of the natural lens from the lens capsule 30, the IOL device 100 is introduced into the lens capsule 30 through the small incision. Once the IOL device 100 is positioned within the lens capsule 30, with the anterior lens 110 being centered about the optical axis A-A, the enclosed cavity 105 of the IOL device is filled with an appropriate fluid through a self-sealing valve disposed on the IOL. The volume of fluid used to fill the enclosed cavity 105 is understood to be tailored based size of the lens capsule 30 for each patient. In a desired embodiment, the volume is sufficient so as to permit engagement of the peripheral portion 130 with the zonule fibers 40 and the ciliary muscles 50.

The eye's natural mechanism of accommodation is reflected by the changes in the shape of the lens and thus the extent to which it refracts light. FIGS. 5-6 show how the IOL device 100 changes its shape in response to the accommodative functions of the eye.

FIG. 5 shows the eye in a relatively accommodated state, as may be the case when the eye is focusing on a nearby object. In an accommodated state, the ciliary muscles 50 contract, and the contraction of the ciliary muscles 50 cause them to move in an anterior direction. This, in turn, reduces the stress on the zonule fibers 40, thereby lessening the stress exerted by the zonule fibers 40 on the lens capsule 30. The IOL device 100 thereupon undergoes elastic recovery and rebounds to a more rounded, biconvex shape.

FIG. 6 shows the eye in a relatively unaccommodated state, as may be the case when the eye is focusing at a distance. In an accommodated state, the ciliary muscles 50 relax, thereby increasing the diameter of its opening and causing the zonule fibers 40 to pull away from the optical axis A-A. This, in turn, causes the zonule fibers 40 to radially pull on the periphery of the lens capsule 30 and cause the IOL device 100 to assume a flatter shape. As the shape of the lens capsule 30 is flattened, its ability to bend or refract light entering the pupil is reduced. Thus, in an unaccommodated state, the IOL device 100 has a flatter geometry.

FIG. 7 illustrates another embodiment of the IOL device 200, which provides a lower profile design that is specifically adapted to mitigate undesired flattening of the rounded posterior surface during accommodation that may result from the anterior pressure exerted by the vitreous. The IOL device 200 is depicted as comprising an anterior lens 210 and a posterior surface 250. An articulating member couples the anterior lens 210 and the posterior surface 250. Hinges 225, 245 disposed about the anterior lens 210 and the posterior surface 250 permit a greater displacement of the anterior lens 210 and posterior surface 250 away from one another when the eye is in an accommodated state. Significantly, the posterior surface 250 of the IOL device 200 comprises a curved stepped-in portion 260 that surrounds the optical axis. The stepped-in portion 260 is coupled to the outer circumferential region 252 of the posterior surface by a circumferential ring member 254 that projects into the enclosed cavity 205. The configuration of the stepped-in portion 260 not only results in a lower profile IOL device 200, but also resists flattening that may result from the anterior pressure that may be exerted by the vitreous. While FIG. 7 depicts the circumferential ring member 254 has having two angled corners 254a, 254b, it is understood that the two angled corners 254a, 254b may be curved or rounded.

FIG. 8 illustrates a further embodiment of the IOL device 300, which also provides a lower profile design and resists the potential flattening of the posterior surface along the optical axis by anterior pressure from the vitreous. The IOL device 300 is depicted as comprising an anterior lens 310 and a posterior surface 350 that is coupled together by an articulating member having an anterior arm 320, a peripheral portion 330, and a posterior arm 340. A pair of hinges 325, 345 is again provided to permit movement by the anterior lens 310 and the posterior surface 350. In contrast to the previous embodiments of the IOL device shown and described herein, a concave central portion 356 is provided surrounding the optical axis. The concave central portion 356 is coupled to a outer circumferential portion 352 and a hinge 354 is provided therebetween to permit the concave central portion 356 to increase and decrease its radius of curvature in response to accommodation. While FIG. 8 depicts the hinge 354 has having an angled corner, it is understood that the hinge 354 may be curved or rounded. The concave central portion 356 therefore moves in the same direction along the optical axis as the anterior lens 310 during the accommodation process.

Figure 9:
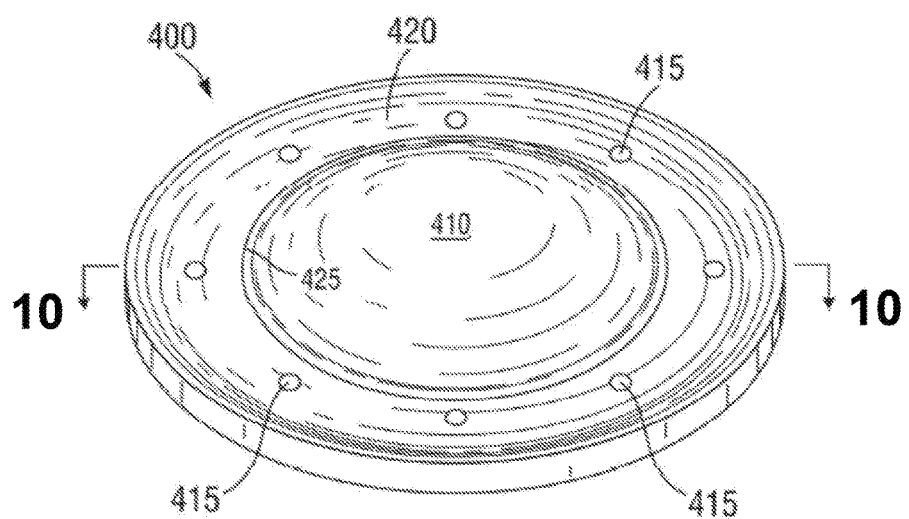
FIG. 9 is a top perspective view of yet another embodiment of an IOL device comprising a plurality of apertures.

FIGS. 9-10 depict yet another embodiment of the IOL device 400 which permits for the changes in the volume of fluid that is contained within the internal cavity 405. As shown in FIG. 9, a plurality of holes 415 may be disposed on the anterior member 420 of the articulating member. While FIG. 9 depicts that the holes 415 are disposed circumferentially around the anterior lens 410, the number and location of the holes is not so limited. The advantage of providing the plurality of holes 415 is that displacement of the fluid contained within the internal cavity 405 of the IOL device 400 permits a greater range of accommodation of the IOL device 400.

Figure 10A:
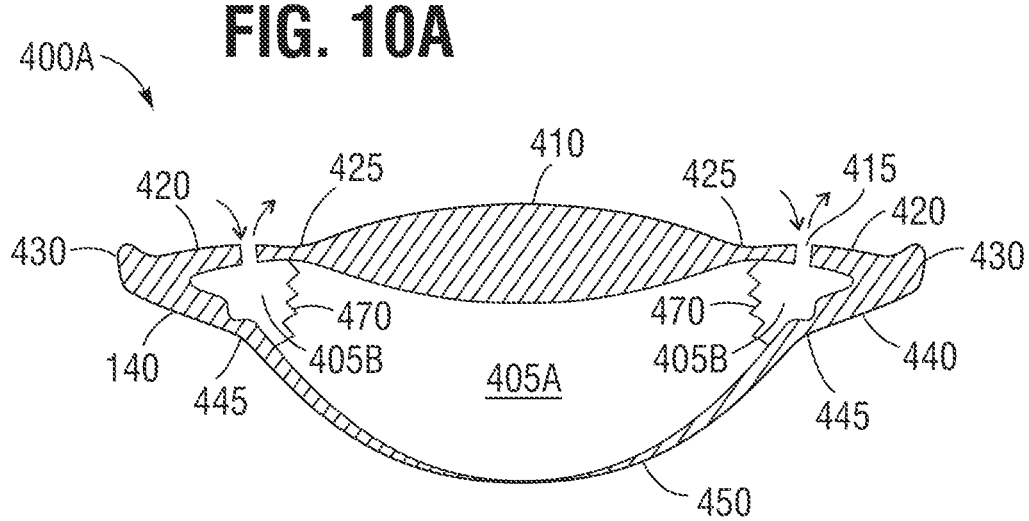
FIG. 10A is a cross-sectional view of one embodiment of the IOL device of FIG. 9, taken along the 10-10 axis of FIG. 9.

In one embodiment, as shown in FIG. 10A, the IOL device 400 comprises two separate internal cavities 405A, 405B, which are not in fluid communication with one another. A constant volume of fluid is maintained within the inner cavity 405A, whereas the volume of fluid contained within the outer cavity 405B is allowed to change in response to the accommodative forces which are applied to the IOL device 400. Fluid in the outer cavity 405B is permitted to exit and enter into the outer cavity 405B depending on the geometric configuration of the IOL device 400. Thus, when IOL device 400 takes on a flatter configuration as would be typical when the eye is not accommodated, displacement of the fluid from the outer cavity 405B will facilitate the IOL device 400 to take on the flatter configuration. A corrugated bellow 470 may be provided to separate the inner and outer cavities 405A, 405B.

Figure 10B:
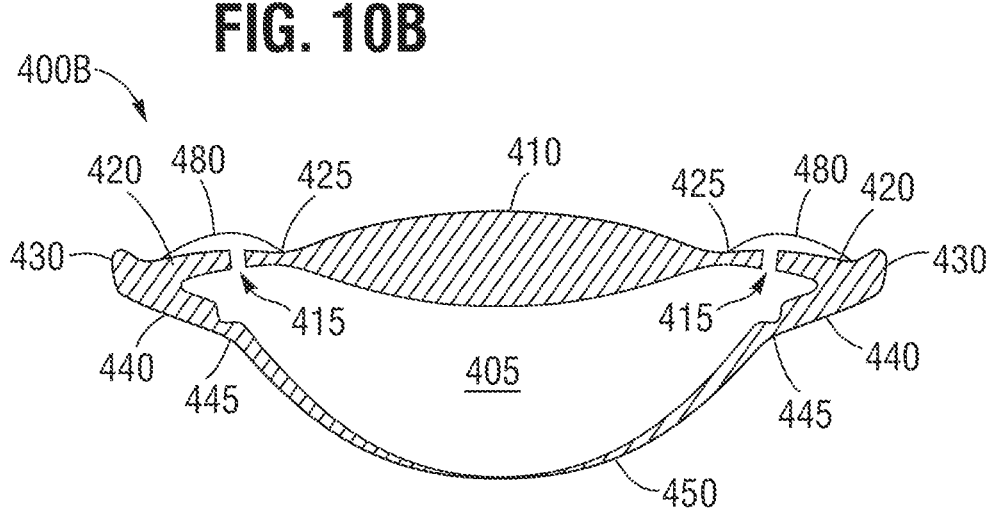
FIG. 10B is a cross-sectional view of another embodiment of the IOL device of FIG. 9, taken along the 10-10 axis of FIG. 9.
Figure 10C:
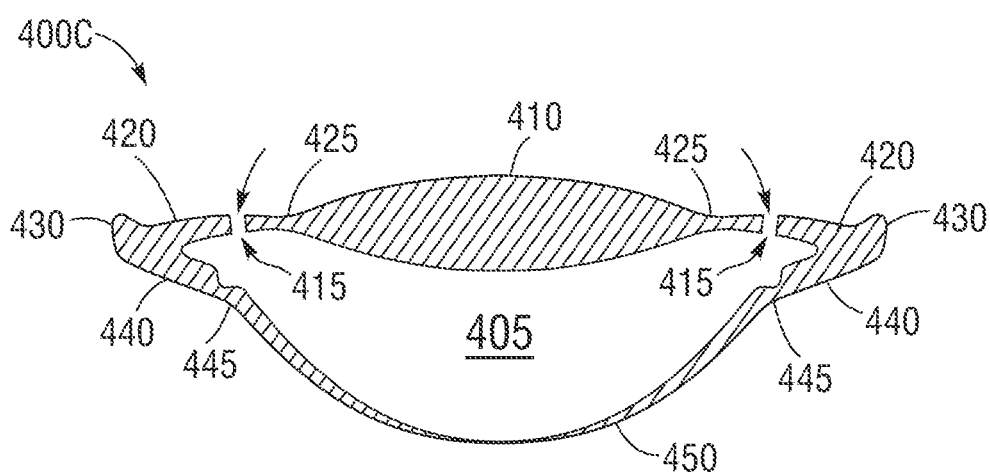
FIG. 10C is a cross-sectional view of yet another embodiment of the IOL device of FIG. 9, taken along the 10-10 axis of FIG. 9.

Alternatively and as shown in FIGS. 10B and 10C, the IOL device 400 may maintain a single internal cavity 405.

In cases where the fluid contained within the internal cavity 405 is not sufficiently biocompatible or is biohazardous, FIG. 10B further provides for an external membrane 480 that is disposed over the plurality of holes 415 to ensure that the fluid does not escape into and becomes absorbed by the body. Thus, the external membrane 480, while permitting a range of dimensional changes for the IOL device 400, also maintains a sufficient barrier to prevent the fluid from discharging into the body.

In cases where the fluid is biocompatible, i.e., saline solution, the IOL device 400 depicted in FIGS. 10A and 10C may be used. With respect to FIG. 10A, it is further noted that while the fluid contained in the outer cavity 405B is required to be biocompatible, the fluid contained in the inner cavity 405A is not held to the same requirement. In the embodiment depicted in FIG. 10C, where there is a single inner cavity 405, it is understood that the fluid contained within the inner cavity 405 is fluid communication with the fluid outside of the IOL 400. Therefore, in the embodiment depicted in FIG. 10C, it is desirable that the fluid be substantially, if not completely, biocompatible.

Figure 11A:
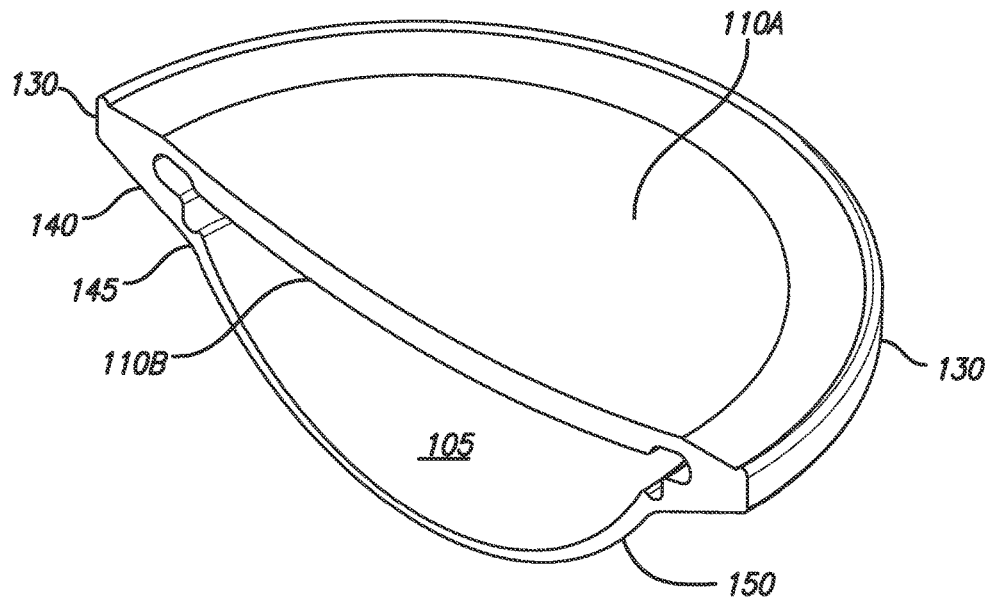
FIG. 11A is a perspective cross-sectional view of the IOL device in which the top surface of the anterior lens is concave and the bottom surface of the anterior lens is convex.
Figure 11B:
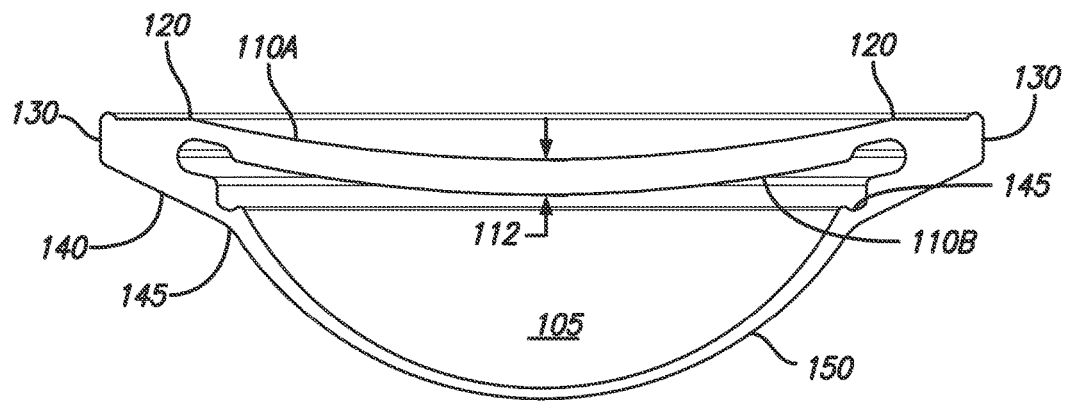
FIG. 11B is a cross-sectional view of the IOL device in which the anterior lens of FIG. 11A is thickened.
Figure 13:
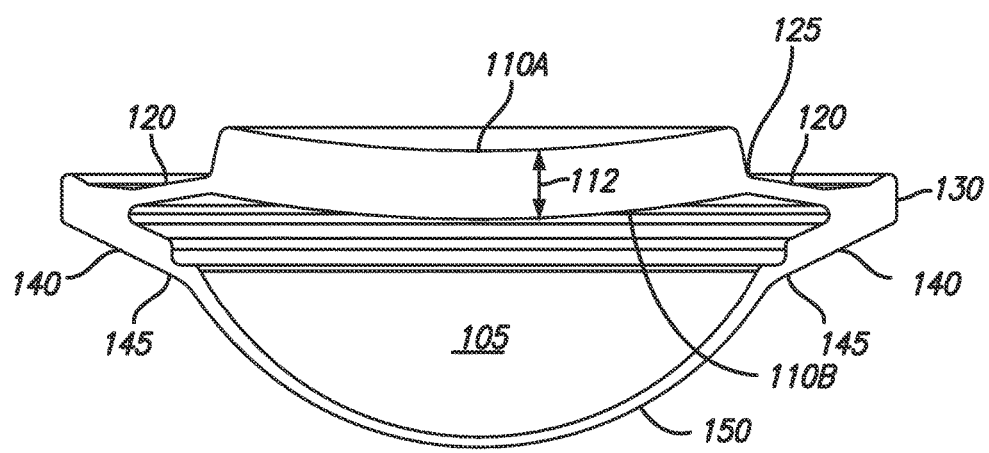
FIG. 13 is a cross-sectional view of yet a further embodiment of an IOL device in which the anterior lens is thickened.
Figure 14:
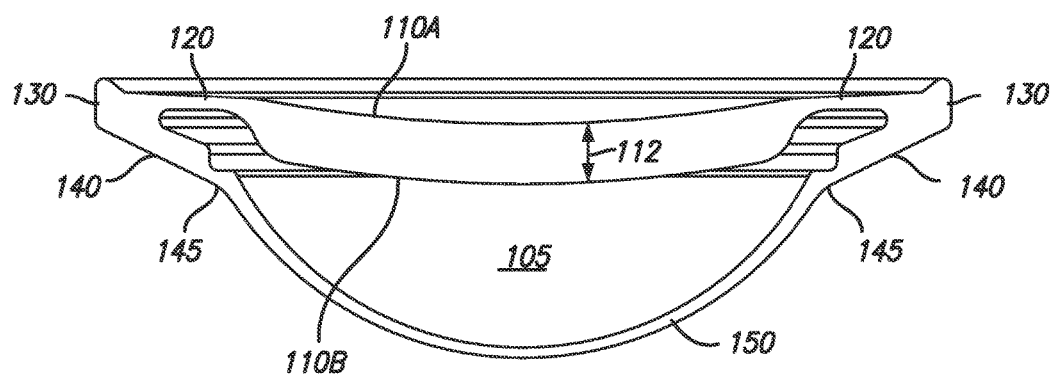
FIG. 14 is a cross-sectional view of yet another embodiment of an IOL device in which the anterior lens is thickened.

While FIGS. 1-10 depict the anterior lens 110 of the IOL device 100 as being biconvex, it is understood that the anterior lens 110 may be biconcave or have a combination of a convex or concave outer surface and an concave or convex inner surface. FIGS. 11A-B and 13 depict the anterior lens as having an outer concave surface 110A and an inner convex surface 110B. The difference between FIG. 11A, on the one hand, and FIGS. 11B and 14, on the other hand, is the thickness of the anterior lens from the outer surface 110A to the inner surface 110B, with FIGS. 11B and 13 showing an anterior lens having a thicker cross-section 112 as compared to the anterior arm 120. In the embodiment shown in FIGS. 11A-B and 13, the presence of anterior hinges is optional since both the anterior lens 110 and the posterior portion 150 are displaced in the same posterior direction when opposing sides of the peripheral portion 130 move towards one another. Moreover, because the anterior lens 110 is not being displaced in the anterior direction, the anterior arms 120 similarly need not be projected in the substantially anterior direction but rather slightly towards the posterior surface 150. As shown in FIG. 13, the anterior lens 110 may be thickened in the posterior direction so as to provide a substantially continuous anterior surface of the IOL device.

Figure 12:
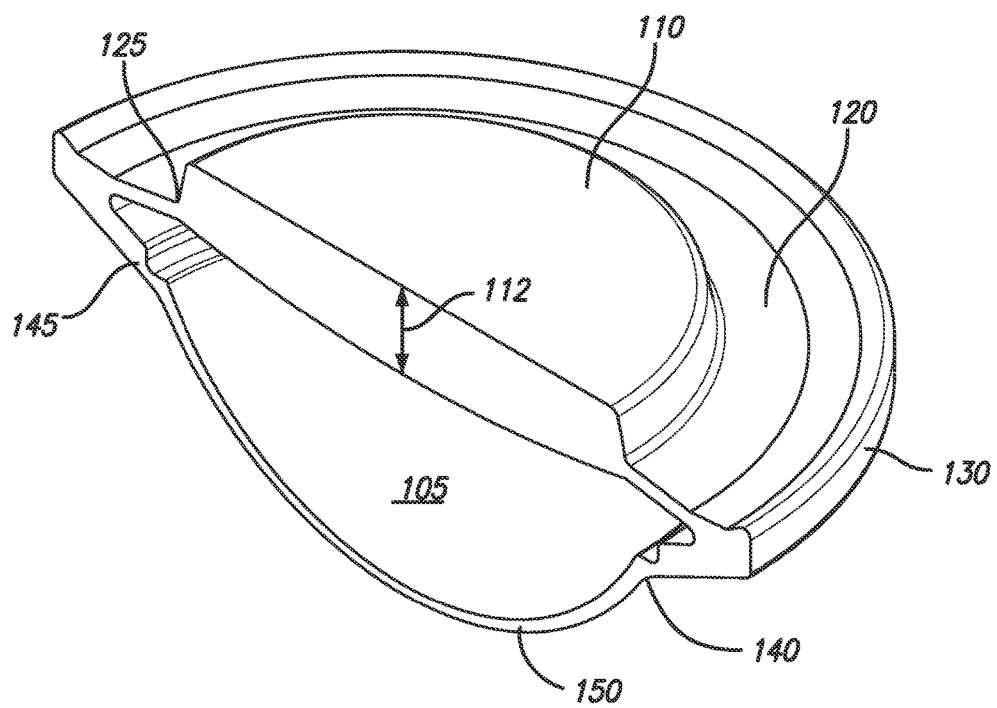
FIG. 12 is a cross-sectional view of yet another embodiment of an IOL device in which the anterior lens is thickened and has a concave exterior surface and a convex interior surface.

FIG. 12 depicts yet another embodiment in which the IOL device comprises an anterior lens 110 having a thickness 112 that protrudes in the anterior direction. In the embodiment depicted in FIG. 12, the anterior lens 110 and the posterior surface 150 move away from one another when opposing sides of the posterior portion 130 are displaced towards one another. Unlike the embodiment depicted in FIG. 13, the embodiment in FIG. 12 depicts the thickness provided anteriorly of the IOL device. The anterior lens 110 again may be biconvex or it may have a concave outer surface 110A and a convex inner surface 110B.

In all of the embodiments described herein, the relative thickness of the anterior lens 110 and the anterior arm 120 and the presence and thickness of the anterior hinge 125 will have an impact on the extent to which the anterior lens 110 is displaced translationally along the optical axis A and also on the extent to which the anterior lens 110 changes in curvature in response to the accommodating forces of the eye. For example, in embodiments where the anterior lens 110 is significantly thicker than either one or both of the anterior arm 120 and/or the anterior hinge 125 (e.g., FIGS. 12-13), the anterior lens 110 is expected to undergo translational displacement along the optical axis A with little, if any, changes in curvature. On the other hand, the anterior lens 110 is likely to undergo changes in curvature more than translational movement along the axis in embodiments where the anterior lens 110 is not thicker than the anterior arm 120 (compare FIGS. 11A and 11B).

The shape of the anterior lens, e.g., biconvex, concave, concave/convex, biconcave, may also be selected based on the refractive index of the fluid selected for the IOL device. For example, if the an anterior lens having a negative power may be more useful to obtain the correct change of power when the IOL device is stretched and relaxed, particularly where the refractive index of the anterior lens 110 and the posterior surface 150 are less than the refractive index of the fluid 105.

Moreover, the angle of the anterior arm 120 may also be configured to determine the extent and manner in which the anterior lens 110 will react to the changes in the eye's accommodating forces. For example, the anterior lens 110 would be expected to move in the direction in which the anterior arm 110 is angled. Thus, where the anterior arm 120 is angled anteriorly relative to a plane that is orthogonal to the optical axis, the anterior lens 110 is also expected to be displaced in the anterior direction when the eye is in an accommodated state. Where the anterior arm 120 is angled posteriorly relative to the same plane, the anterior lens is expected to be displaced in the posterior direction when the eye is in an unaccommodated state.

It is to be understood that the detailed description and specific examples, while indicating preferred embodiments of the present invention, are given by way of illustration and not limitation. Many changes and modifications within the scope of the present invention may be made without departing from the spirit thereof, and the invention includes all such modifications.

What is claimed is:

1. An accommodating intraocular lens (IOL) comprising:
   an anterior lens;
   a flexible posterior surface comprising a concave central portion surrounding an optical axis, wherein the concave central portion is coupled to an outer circumferential portion of the flexible posterior surface;
   an articulating member joining the anterior lens and the posterior surface, the articulating member comprising anterior and posterior arms coupling the anterior lens and the posterior surface, respectively, and a peripheral portion coupled to the anterior and posterior arms, the peripheral portion having a length extending radially away from the anterior and posterior arms and having a thickness that is greater than each of a thickness of the anterior arm and a thickness of the posterior arm; and
   a first posterior flex region disposed about the posterior arm and at a distance from the peripheral portion, the first posterior flex region permitting the flexible posterior surface to articulate relative to the posterior arm, to decrease the radius of curvature of the posterior surface as the peripheral portion on opposing sides of the IOL move toward one another in a first state and to increase the radius of curvature of the posterior surface as the peripheral portion on opposite sides of the IOL move away from one another in a second state, the first posterior flex region having a reduced thickness as compared to each of the posterior arm and the flexible posterior surface.

2. The IOL of claim 1, wherein the articulating member has a wishbone shape and the anterior and posterior arms move away from each other in the first state and move towards each other in the second state.

3. The IOL of claim 1, wherein the articulating member further comprises an anterior flex region between the anterior lens and the anterior arm.

4. The IOL of claim 3, wherein the anterior flex region permits displacement of the anterior lens in an anterior direction when the IOL is in the first state.

5. The IOL of claim 4, wherein the anterior flex region has a reduced thickness as compared to either of the anterior arm and the anterior lens.

6. The IOL of claim 3, wherein both the first posterior flex region and the anterior and posterior flex regions comprise a groove disposed circumferentially about the IOL.

7. The IOL of claim 1, wherein the first posterior flex region is disposed between the flexible posterior surface and the posterior arm.

8. The IOL of claim 1, wherein the peripheral portion defines an outer circumference of the IOL.

9. The IOL of claim 1, wherein the articulating member resiliently biases the IOL in either one of the first state or the second state.

10. The IOL of claim 1, further comprising a second posterior flex region between the concave central portion and the outer circumferential portion of the posterior surface.

11. An accommodating intraocular lens (IOL) comprising:
an anterior lens;
a posterior surface comprising a concave central portion surrounding an optical axis, wherein the concave central portion is coupled to an outer circumferential portion of the flexible posterior surface;
an articulating member joining the anterior lens and the posterior surface to form an enclosed cavity, the articulating member comprising anterior and posterior rings coupling the anterior lens and the posterior surface, respectively, to a peripheral portion, the peripheral portion having a length extending radially away from the anterior and posterior rings and a thickness that is greater than a thickness of the anterior ring and a thickness of the posterior ring;
a first hinge disposed between the anterior lens and the anterior ring, the first hinge having a reduced thickness as compared to each of the anterior ring and the anterior lens; and
a second hinge disposed between the posterior surface and the posterior ring, the second hinge having a reduced thickness as compared to each of the posterior ring and the posterior surface.

12. The IOL of claim 11, wherein the second hinge is a circumferential groove defining a circular area having a diameter.

13. The IOL of claim 12, wherein the IOL is configured to articulate between a first state and a second state.

14. The IOL of claim 13, wherein in the first state, the peripheral portion on opposing sides of the IOL move towards one another to cause a decrease in the radius of curvature of the posterior surface.

15. The IOL of claim 14, wherein in the second state, the peripheral portion on opposing sides of the IOL move away from one another to increase the radius of curvature of the posterior surface.

16. The IOL of claim 11, further comprising a third hinge between the concave central portion and the outer circumferential portion of the posterior surface.

17. An accommodating intraocular lens (IOL) configured for implantation in a lens capsule of a patient's eye, the IOL comprising:
a refractive anterior lens;
a deformable posterior membrane comprising a concave central portion surrounding an optical axis, wherein the concave central portion is coupled to an outer circumferential portion of the posterior membrane;
an articulating member joining the refractive anterior lens and the posterior membrane to form an enclosed cavity, the articulating member comprising an anterior portion, a posterior portion, and a peripheral portion coupled to the anterior and posterior portions, the peripheral portion having a length extending radially away from the anterior and posterior portions and having a thickness that is greater than each of a thickness of the anterior portion and a thickness of the posterior portion; and
a first flex region disposed about the posterior portion and at a distance from the peripheral portion, the first flex region having a reduced thickness as compared to each of the posterior membrane and the posterior portion;
wherein one end of the anterior portion is coupled to the anterior lens and another end of the anterior portion is coupled to the peripheral portion;
wherein one end of the posterior portion is coupled to the posterior membrane and another end of the posterior portion is coupled to the peripheral portion;
wherein in a first state, opposing sides of the peripheral portion move toward one another to displace the anterior lens in an anterior direction along an optical axis and cause the radius of curvature of the posterior membrane to decrease; and
wherein in a second state, opposing sides of the peripheral portion move away from one another, to displace the anterior lens in a posterior direction along the optical axis and cause the radius of curvature of the posterior membrane to increase.

18. The IOL of claim 17, further comprising a second flex region between the concave central portion and the outer circumferential portion of the posterior surface.

* * * * *